(12) United States Patent
Heffels

(10) Patent No.: US 11,060,969 B2
(45) Date of Patent: Jul. 13, 2021

(54) GAS ANALYZER

(71) Applicant: SIEMENS AKTIENGESELLSCHAFT, Munich (DE)

(72) Inventor: Camiel Heffels, Stutensee-Büchig (DE)

(73) Assignee: Siemens Aktiengesellschaft, Munich (DE)

( * ) Notice: Subject to any disclaimer, the term of this patent is extended or adjusted under 35 U.S.C. 154(b) by 105 days.

(21) Appl. No.: 16/498,783

(22) PCT Filed: Mar. 29, 2018

(86) PCT No.: PCT/EP2018/058230
§ 371 (c)(1),
(2) Date: Sep. 27, 2019

(87) PCT Pub. No.: WO2018/178306
PCT Pub. Date: Oct. 4, 2018

(65) Prior Publication Data
US 2021/0109014 A1 Apr. 15, 2021

(30) Foreign Application Priority Data
Mar. 31, 2017 (DE) .................. 20 2017 001 743.1

(51) Int. Cl.
*G01N 21/31* (2006.01)
*G01N 33/00* (2006.01)

(52) U.S. Cl.
CPC ......... *G01N 21/31* (2013.01); *G01N 33/0037* (2013.01); *G01N 33/0042* (2013.01);
(Continued)

(58) Field of Classification Search
CPC ...... G01N 21/31; G01N 21/314; G01N 21/85; G01N 33/0037; G01N 33/0042;
(Continued)

(56) References Cited

U.S. PATENT DOCUMENTS

| 6,791,689 B1 | 9/2004 | Weckström |
| 9,000,374 B2 | 4/2015 | Parks, II et al. |
| (Continued) | | |

FOREIGN PATENT DOCUMENTS

| DE | 19814969 | 10/1999 |
| DE | 102013107422 | 3/2014 |
| (Continued) | | |

OTHER PUBLICATIONS

Thorlabs "drawing projection" 2015 (Year: 2015).*
(Continued)

*Primary Examiner* — Maurice C Smith
(74) *Attorney, Agent, or Firm* — Cozen O'Connor

(57) ABSTRACT

A gas analyzer for measuring two gas components of a measuring gas includes two light-emitting diodes, a beam splitter, a measuring chamber through which the measuring gas circulates, a measurement detector, a reference detector, and a control and evaluation device for controlling the light-emitting diodes in an alternating manner and for evaluating the signals supplied by the measurement detector and the reference detector in terms of measuring results for the two gas components, wherein the beam splitter is arranged in a rectangular metal block, where the measuring chamber is formed as a long hollow body consisting of metal and open on both sides, the measurement detector is held on a detector block consisting of metal, and where the rectangular metal block and the detector block are interconnected via tension rods between which the measuring chamber is clamped.

12 Claims, 2 Drawing Sheets

(52) U.S. Cl.
CPC ........... *G01N 2201/0231* (2013.01); *G01N 2201/062* (2013.01); *G01N 2201/0633* (2013.01); *G01N 2201/0636* (2013.01)

(58) Field of Classification Search
CPC ....... G01N 2201/062; G01N 2201/121; G01N 2201/0625; G01N 21/33; G01N 2021/8578; G02B 27/10
See application file for complete search history.

(56) References Cited

U.S. PATENT DOCUMENTS

| | | |
|---|---|---|
| 2014/0034854 A1 | 2/2014 | Reiter |
| 2016/0054294 A1 | 2/2016 | Rihani et al. |
| 2016/0266032 A1 | 9/2016 | Thomas et al. |

FOREIGN PATENT DOCUMENTS

| | | | |
|---|---|---|---|
| DE | 102014107342 | 11/2015 | |
| DE | 102017213 A1 * | 10/2017 | ............ G01N 21/03 |
| DE | 102016108267 | 11/2017 | |
| JP | WO2015/181879 A1 * | 4/2017 | ............ G01N 21/33 |
| WO | WO 2016/145066 | 9/2016 | |
| WO | WO2014/157282 | 2/2017 | |
| WO | WO2014/162537 | 2/2017 | |

OTHER PUBLICATIONS

Higashi Ryoichi et al: "A NOx and SO2 gas analyzer using deep-UV and violet light-emitting diodes for continuous emissions monitoring systems", Proc. SPIE 9003, Light-Emitting Diodes: Materials, Devices, and Applications for Solid State Lighting XVIII, 90031F, pp. 1-6; 2014.

T. Wu, et al: Incoherent broadband cavity enhanced absorption spectroscopy for in situ measurements of N02 with a blue light emitting diode2. In: Applied Physics B Lasers and Optics; 94; pp. 85-94. vol. 10.1007/s00340-008-3308-8.

Gomez A L et al: "Fast response cavity enhanced ozone monitor", Atmospheric Measurement Techniques, vol. 6, No. 2, 2013, pp. 487-494, XP055476579, DOI: 10.5194/amt-6-487-2013, pp. 488, right column, line 14—pp. 489, left column, line 25, Figure 1.

Thorlabs: "30 mm Cage Components", 2016, XP055477282, found on Internet: URL:https://web.archive.org/web/20160401210617/ https://www.thorlabs.de/navigation.cfm?guideid=2004 [found on May 22, 2018], the whole document.

Anonymous: "GCH25-75 Gas Cell Oven", XP055411168, found on Internet: URL:https://www.thorlabs.com/drawings/1d91e8af276bf034-D5CF10CC-92C2-AA6A-6E14871368ECB5E2/GCH25-75-Manual.pdf, [gefunden am Sep. 28, 2017] the whole document; 2010.

PCT International Search Report dated May 23, 2018 based on PCT/EP2018/058230 filed Mar. 29, 2018.

* cited by examiner

GAS ANALYZER

CROSS-REFERENCE TO RELATED APPLICATIONS

This is a U.S. national stage of application No. PCT/EP2018/058230 filed Mar. 29, 2018. Priority is claimed on German Application No. 202017001743.1 filed Mar. 31, 2017, the content of which is incorporated herein by reference in its entirety.

BACKGROUND OF THE INVENTION

1. Field of the Invention

The invention relates to a gas analyzer for measuring two gas components in a measurement gas.

2. Description of the Related Art

A conventional gas analyzer for measuring nitrogen oxides and sulfur dioxide in an exhaust gas is known from Ryoichi Higashi et al.: "A NOx and SO2 gas analyzer using deep-UV and violet light-emitting diodes for continuous emissions monitoring systems", Proc. SPIE 9003, Light-Emitting Diodes: Materials, Devices, and Applications for Solid State Lighting XVIII, 90031F (Feb. 27, 2014), where nitrogen monoxide contained in the exhaust gas is converted into nitrogen dioxide that can be measured using the gas analyzer, such that the concentration of nitrogen dioxide determined in the gas analyzer is a measure of the concentration of nitrogen oxides in the exhaust gas.

In such a conventional gas analyzer, a first light-emitting diode with an emission wavelength of approximately 280 nm in the absorption range of sulfur dioxide and a second light-emitting diode with an emission wavelength of approximately 400 nm in the absorption range of nitrogen dioxide are arranged close to one another in an LED array. Their light is shaped via a collimator lens to form a parallel beam of light that penetrates a measurement chamber and is then focused onto a measurement detector. With a beam splitter between the collimator lens and the measurement chamber, some of the light is directed onto a reference detector.

SUMMARY OF THE INVENTION

It is an object of the invention to provide a gas analyzer for measuring two gas components in a measurement gas, where the gas analyzer has a simple and stable structure.

This and other objects and advantages are achieved in accordance with the invention a gas analyzer for measuring two gas components in a measurement gas, with a first light-emitting diode that emits light with a first wavelength in the range of an absorption line of the one, first gas component, with a second light-emitting diode that emits light with a second wavelength in the range of an absorption line of the other, second gas component, with a beam splitter, with a measurement chamber through which the measurement gas can flow, with a measurement detector, with a reference detector and with a control and evaluation device for controlling the light-emitting diodes in an alternating manner and for evaluating the signals supplied by the measurement detector and the reference detector to form measurement results for the two gas components, where the beam splitter is arranged in a rectangular metal block comprising a base, a top surface and four lateral surfaces in the intersection region of two bores that extend between the respective opposing lateral surfaces, the two light-emitting diodes are arranged on two adjoining lateral surfaces and the measurement chamber and the reference detector are arranged on the other two adjoining lateral surfaces of the metal block that each oppose the bores, the measurement chamber is formed as an elongated hollow body open on both sides and consisting of metal, with two lateral access openings for the measurement gas, the measurement detector is held on a detector block consisting of metal and containing an opening and the rectangular metal block and the detector block are connected to one another via tension rods and the measurement chamber is clamped between them.

The inventive gas analyzer has a compact structure. The measurement chamber, the metal block containing the beam splitter, and the detector block are in close thermal contact because of the bracing via the connecting rods, such that the light-emitting diodes and detectors arranged thereon are also at the same temperature level.

The tension rods have threads at their ends or are structured threaded rods. The tension rods can be connected directly to the rectangular metal block and the detector block or, as explained further below, can act on these indirectly via plates externally abutting the metal block and detector block.

The hollow body forming the measurement chamber can be formed as a hollow profile body or can contain a through bore that is milled into a longitudinal body consisting of metal.

To simplify the mounting and adjustment of the beam splitter, the rectangular metal block preferably contains, on its top surface, an opening extending into the intersection region of the two bores, in which opening an insert accommodating the beam splitter is inserted.

The light-emitting diodes, the measurement detector and/or the reference detector are preferably arranged on plates that are mounted either directly or if appropriate with the intermediate layering of a spacer frame on the respective lateral surfaces of the rectangular metal block or, in the case of the reference detector, on the side of the detector block facing away from the measurement chamber. The plates can be individually mounted on the metal block or the detector block, e.g., can be screwed thereto. In the case of the measurement detector and the light-emitting diode opposing it in a straight line, the aforementioned connecting rods can run through holes or bores in the detector block, the metal block and the plates carrying the measurement detector and the light-emitting diode and can be screwed thereto on the sides of the plates facing outward, such that the detector block, the measurement chamber and the metal block are clamped between the plates.

With the help of collimator lenses, the light of the light-emitting diodes is preferably shaped into a parallel beam of light which, with the help of focusing lenses, is focused onto the reference detector or after penetrating the measurement chamber onto the measurement detector. The associated design work can in particular be minimized if the collimator lenses with their lens mounts are inserted in the bores on the lateral surfaces of the metal block facing the light-emitting diodes and the focusing lenses with their lens mounts are inserted in the bore on the lateral surface of the metal block opposing the reference detector and in the opening of the detector block opposing the measurement detector. Preferably, all inserted lenses have the same technical specification.

By heating the measurement chamber, for example, to 52° C., it is possible to prevent water vapor contained in the measurement gas from condensing out. For this purpose, at least one electric heating element is preferably mounted on the external wall of the hollow body forming the measurement chamber. A transistor is particularly suitable for this, and simultaneously serves as a heating element and temperature sensor, such that no elaborate regulation is necessary to keep the temperature constant. Because of the good thermal contact, the temperature of the light-emitting diodes and detectors is controlled via the rectangular metal block and the metal detector block, such that measurement errors caused by changing temperatures can be prevented. The preferred placement of the gas analyzer in a container that is made of insulating material, such as rigid polystyrene foam or expanded polypropylene (EPP), and that consists of a shell-shaped lower part and a shell-shaped or cover-shaped upper part also serves to keep the temperature constant.

The measurement chamber can be closed in a known manner at both ends with flat windows or alternatively with semitransparent concave mirrors which, between them, form a resonator to extend the absorption path. The corresponding measurement procedure "Incoherent Broad-Band Cavity-Enhanced Absorption Spectroscopy" (IBBCEAS) combines the simplicity and reliability of traditional absorption spectroscopy with the sensitivity of "cavity-ring-down" spectroscopy.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

BRIEF DESCRIPTION OF THE DRAWINGS

The invention is explained below based on exemplary embodiments and with reference to the figures in the drawings, in which.

DETAILED DESCRIPTION OF THE EXEMPLARY EMBODIMENTS

Figure 1:
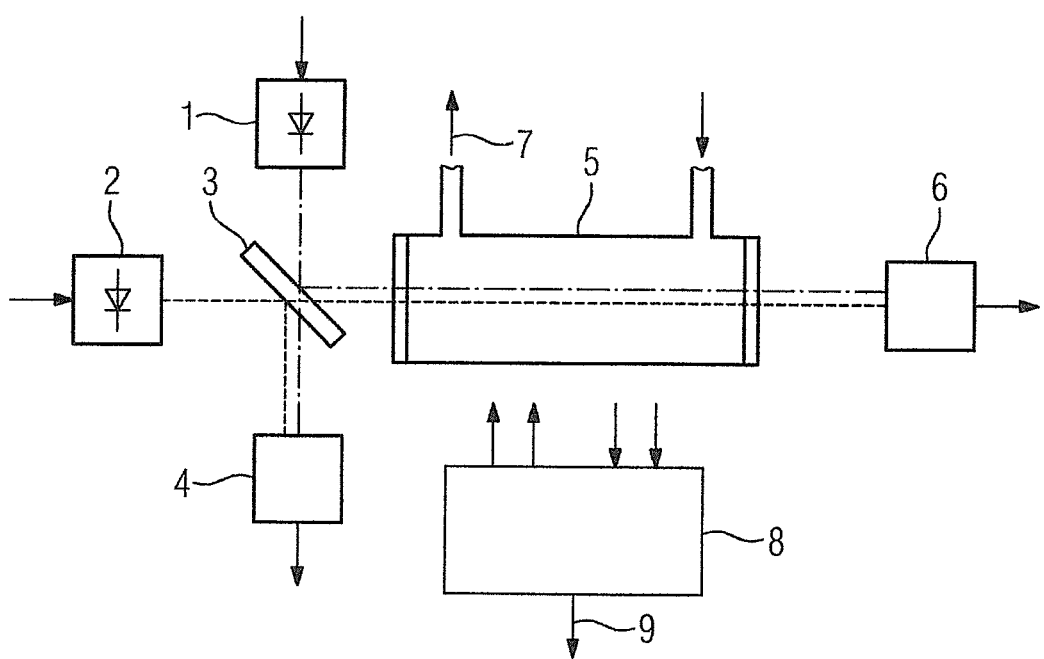
FIG. 1 shows a greatly simplified block diagram of the gas analyzer in accordance with the invention.

FIG. 1 shows a gas analyzer which contains a first light-emitting diode 1 with an emission wavelength of 285 nm (+/−10 nm) in the absorption range of sulfur dioxide and a second light-emitting diode 2 with an emission wavelength of 400 nm (+/−20 nm) in the absorption range of nitrogen dioxide. The light from both light-emitting diodes 1, 2 is conducted directly via a beam splitter 3 onto a reference detector 4 and though a measurement chamber 5 onto a measurement detector 6. A measurement gas 7, the sulfur dioxide and nitrogen dioxide content of which is to be measured, flows through the measurement chamber 5. A control and evaluation device 8 controls the light-emitting diodes 1, 2 in an alternating manner and evaluates the signals supplied by the measurement detector 6 and the reference detector 4 to form a measurement result 9 for the sulfur dioxide and nitrogen dioxide content of the measurement gas 7. The signal supplied by the measurement detector 6 is dependent on the wavelength-specific absorption by the two gas components of interest and thus their concentration, and is normalized with the signal from the reference detector.

Figure 2:
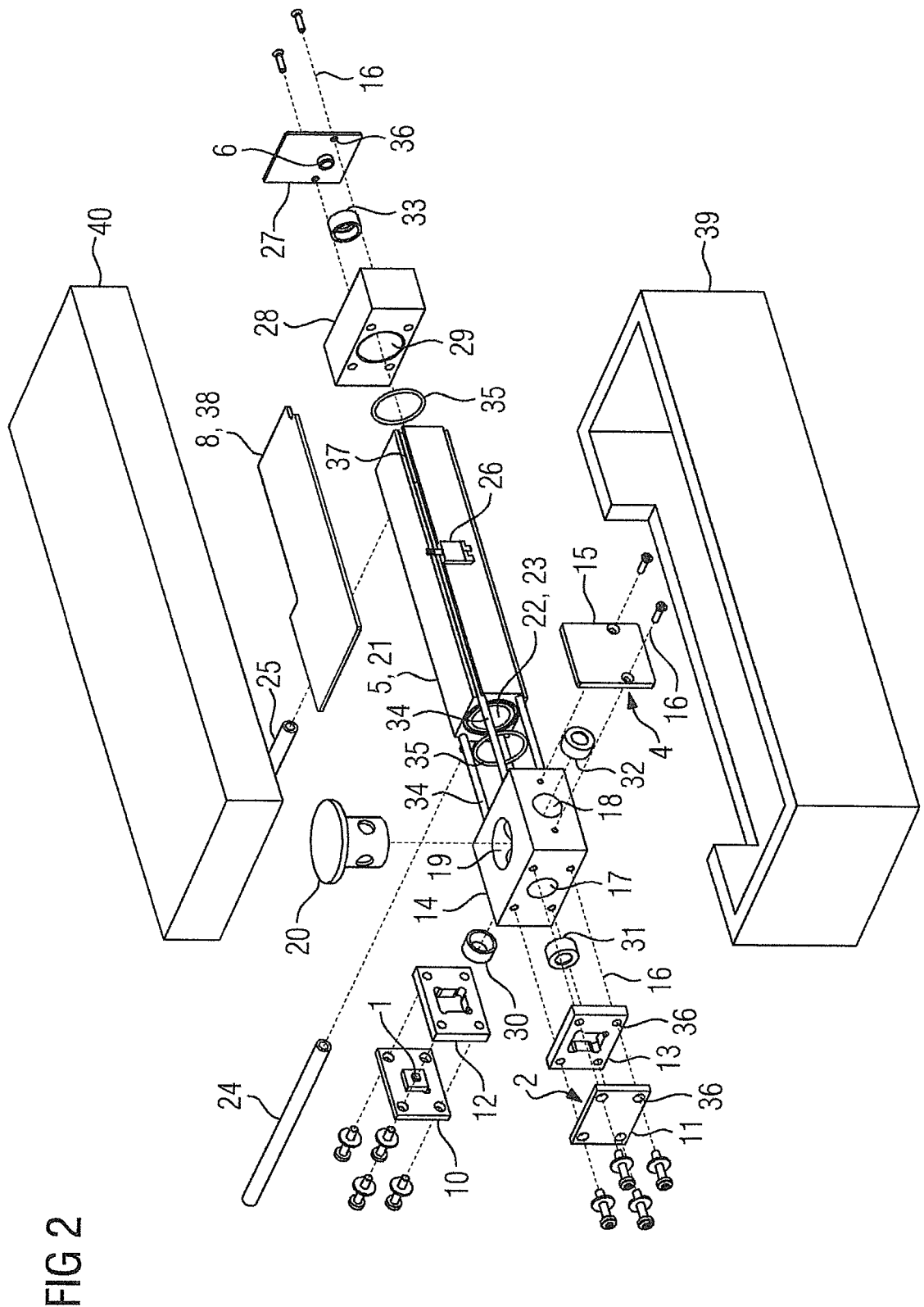
FIG. 2 shows a perspective exploded view of the inventive gas analyzer of FIG. 1.

FIG. 2 shows the light-emitting diode 1 mounted on a plate 10 and a structurally identical plate 11 upon which the light-emitting diode 2 (which is here concealed) is mounted. Both plates 10, 11 are mounted via spacer frames 12, 13 on two lateral surfaces, adjoining one another at right angles, of a rectangular metal block 14 consisting, for example, of aluminum. On the lateral surface facing away from the light-emitting diode 1 a plate 15 with the reference detector 4 (likewise concealed here) is mounted on the metal block 14. The mounting is effected using screw connections, which are indicated by dashed lines 16. The metal block 14 is penetrated by two bores 17, 18 that extend between the respectively opposing lateral surfaces. On its top surface, the metal block 14 contains a round opening 19 that extends into the intersection region of the two bores 17, 18. The beam splitter 3 (not visible here) is arranged in a substantially cylindrical insert 20 that is inserted in the opening 19. By rotating the insert 20, the beam splitter 3 can be adjusted with respect to the axes of the bores 17, 18 extending at right angles. The beam splitter 3 is preferably what is known as a polka-dot beam splitter, in which a transparent carrier plate is metalized with metal points in the surface ratio of 50%.

On the lateral surface of the metal block 14 facing away from the light-emitting diode 2, the measurement chamber 5 abuts the metal block 14 and is formed as an elongated, here rectangular, hollow body 21 consisting of metal, e.g., aluminum, which is open on both sides. The hollow body 21 itself can be formed as a hollow profile body or can contain a machined through bore 22 which is closed on both sides by windows (only the window 23 is visible here). Alternatively, the measurement chamber 5 can be closed with semitransparent concave mirrors that form a resonator to extend the absorption path. The measurement chamber 5 has, on the side here facing away from the viewer, two access openings with terminals for two gas lines 24, 25, via which the measurement gas 7 can be supplied or discharged. Two heating elements are attached to the external wall of the measurement chamber 5 at opposing points, of which only one heating element 26 in the form of a transistor can be seen here, which together with the other heating element is controlled or regulated by the control and evaluation device 8 to keep the temperature of the measurement chamber 5 constant.

The measurement detector 6 is arranged on a plate 27 and is mounted therewith on a rear side of a metal detector block 28, the front side of which abuts the end face of the measurement chamber 5 facing away from the metal block 14 with the beam splitter 3. Extending between the front and rear side of the detector block 28 is an opening 29 that is aligned with the bore 22 of the measurement chamber 5 and the bore 17 in the metal block 14.

Collimator lenses 30, 31 with the lens mounts surrounding them are inserted in the bores 17, 18 on the lateral surfaces of the metal block 14 facing the light-emitting diodes 1, 2. Likewise, focusing lenses 32, 33 with the lens mounts surrounding them are inserted in the bore 18 on the lateral surface of the metal block 14 opposing the reference detector 4 and in the opening 29 on the rear side of the detector block 18. The collimator lenses 30, 31 shape the light emitted by the light-emitting diodes 1, 2 into a parallel beam of light which, with the help of the focusing lenses, is focused onto the reference detector 4 or after penetrating the measurement chamber 5 onto the measurement detector 6.

The metal block 14 containing the beam splitter 3, the measurement chamber 5 and the detector block 27 are braced with one another via four connecting rods 34 that have threads at their ends and are screwed to the two plates 11 and 27 there and at the outward facing sides of said plates 11 and 27. Sealing rings 35 are arranged in the region of the windows 23 between the measurement chamber 5 and the metal block 14 or the detector block 28. The connecting rods or tension rods 34 extend in the plates 11, 27, the spacer frame 13, the metal block 14 and the detector block 28 through corresponding holes or bores 36, whereas they extend along the measurement chamber 5 in grooves 37 that are formed on the external wall of the hollow body 21, here on its longitudinal edges.

The control and evaluation device 8 is arranged on a board 38 that is arranged above the measurement chamber 5.

The gas analyzer is accommodated in a container made of rigid polystyrene foam that consists of a shell-shaped lower part 39 and a shell-shaped or cover-shaped upper part 40.

The plates 10, 11, 15, 27 carrying the light-emitting diodes 1, 2 and detectors 4, 6 are not necessarily to be understood as single plates. They can also respectively involve a combination of, e.g., two single plates, where the one plate is formed as a circuit board that directly carries the light-emitting diode or the detector and has terminals for the electrical connection to the control and evaluation device 8, whereas the other plate, e.g., consisting of metal, receives the circuit board and is otherwise embodied as mechanically stable and serves for mounting.

Thus, while there have been shown, described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

The invention claimed is:

1. A gas analyzer for measuring two gas components in a measurement gas (7), comprising:
    a first light-emitting diode which emits light with a first wavelength in a range of an absorption line of a first gas component of the two gas components;
    a second light-emitting diode which emits light with a second wavelength in the range of an absorption line of a second gas component of the two gas components;
    a beam splitter;
    a measurement chamber, through which measurement gas flows;
    a measurement detector;
    a reference detector; and
    a control and evaluation device for controlling the first and second light-emitting diodes in an alternating manner and for evaluating signals supplied by the measurement detector and the reference detector to form measurement results for the two gas components;
    wherein the beam splitter is arranged in a rectangular metal block comprising a base, a top surface and four lateral surfaces in the intersection region of two bores which extend between respective opposing lateral surfaces;
    wherein the first and second two light-emitting diodes are arranged on two adjoining lateral surfaces and the measurement chamber and the reference detector are each arranged on two other adjoining lateral surfaces of the metal block opposing the bores;
    wherein the measurement chamber is formed as an elongated hollow body open on both sides and consisting of metal, with two lateral access openings for the measurement gas;
    wherein the measurement detector is held on a detector block consisting of metal containing an opening; and
    wherein the rectangular metal block and the detector block are interconnected via tension rods and the measurement chamber is clamped between said rectangular metal block and the detector block.

2. The gas analyzer as claimed in claim 1, wherein the tension rods extend in grooves within an external wall of the hollow body forming the measurement chamber.

3. The gas analyzer as claimed in claim 1, wherein the hollow body forming the measurement chamber is formed as a hollow profile body.

4. The gas analyzer as claimed in claim 2, wherein the hollow body forming the measurement chamber is formed as a hollow profile body.

5. The gas analyzer as claimed in claim 1, wherein the rectangular metal block contains on its top surface an opening extending into the intersection region of the two bores and in that the beam splitter is mounted in an insert inserted in the opening.

6. The gas analyzer as claimed in claim 1, wherein the first and second light-emitting diodes are held on plates which are one of (i) mounted directly on the respective lateral surface of the rectangular metal block and (ii) mounted with the intermediate layering of a spacer frame.

7. The gas analyzer as claimed in claim 1, wherein the measurement detector and reference detector are each held on a plate which is mounted one of (i) directly and (ii) mounted with the intermediate layering of a spacer frame on one of (i) the respective lateral surface of the rectangular metal block and (ii) a side of the detector block facing away from the measurement chamber.

8. The gas analyzer as claimed in claim 1, further comprising:
    collimator lenses inserted in the opposing bores on the lateral surfaces of the metal block facing the light-emitting diodes.

9. The gas analyzer as claimed in claim 1, further comprising:
    a focusing lens inserted in each case in a bore of the opposing bores on a lateral surface of the metal block opposing the reference detector and in the opening of the detector block.

10. The gas analyzer as claimed in claim 1, further comprising:
    at least one electric heating element mounted on an external wall of the hollow body forming the measurement chamber.

11. The gas analyzer as claimed in claim 1, wherein that gas analyzer is arranged in a container made of insulating material consisting of a shell-shaped lower part and a shell-shaped or cover-shaped upper part.

12. The gas analyzer as claimed in claim 1, wherein the measurement chamber is closed with semitransparent concave mirrors which between them form a resonator to extend the absorption path.

* * * * *